(12) United States Patent
Gaytan et al.

(10) Patent No.: US 8,349,767 B2
(45) Date of Patent: Jan. 8, 2013

(54) DEFOLIANT COMPOSITION AND METHOD

(75) Inventors: Jesse H. Gaytan, Valdosta, GA (US);
Joseph A. Hickey, Taft, TX (US);
Osborn J. Turner, IV, Olive Branch, MS (US)

(73) Assignee: Arysta Lifescience North America, LLC, Cary, NC (US)

( * ) Notice: Subject to any disclaimer, the term of this patent is extended or adjusted under 35 U.S.C. 154(b) by 0 days.

(21) Appl. No.: 11/833,786

(22) Filed: Aug. 3, 2007

(65) Prior Publication Data

US 2008/0032891 A1 Feb. 7, 2008

Related U.S. Application Data

(60) Provisional application No. 60/835,463, filed on Aug. 4, 2006.

(51) Int. Cl.
*A01N 43/00* (2006.01)

(52) U.S. Cl. ...................................................... 504/139

(58) Field of Classification Search ........................ None
See application file for complete search history.

(56) References Cited

U.S. PATENT DOCUMENTS

| 6,274,535 | B1 | 8/2001 | Feurer et al. | 504/128 |
|---|---|---|---|---|
| 6,340,655 | B1 * | 1/2002 | Baker | 504/139 |
| 6,444,613 | B1 * | 9/2002 | Feurer et al. | 504/129 |
| 6,455,471 | B1 * | 9/2002 | Gubelmann-Bonneau et al. | 504/133 |
| 6,746,988 | B2 * | 6/2004 | Hopkinson et al. | 504/127 |
| 2003/0161856 | A1 * | 8/2003 | Tandt et al. | 424/405 |

OTHER PUBLICATIONS

Knowles, D.A. (1998). Chemistry and Technology of Agrochemical Formulations. (pp. 47-49, 187-189). Springer—Verlag.*
Haas et al. Influence of polymeric surfactants on pesticidal suspension concentrates: dispersing ability, milling efficiency and stabilization power, Colloids and Surfaces A: Physiochemical and Engineering Aspects 183-185, pp. 785-793, 2001.*

* cited by examiner

*Primary Examiner* — Robert T Crow
*Assistant Examiner* — Thor Nielsen
(74) *Attorney, Agent, or Firm* — Pillsbury Winthrop Shaw Pittman LLP

(57) ABSTRACT

An aqueous suspension or slurry (suspension concentrate) contains a synergistic amount of thidiazuron, diuron and surfactants. The aqueous suspension contains surfactants in amounts to obtain a stable suspension or slurry without the use of organic solvents.

23 Claims, No Drawings

DEFOLIANT COMPOSITION AND METHOD

CROSS-REFERENCE TO RELATED APPLICATION

This application claims the benefit under 35 U.S.C. §119(e) of provisional patent application Ser. No. 60/835,463, filed Aug. 4, 2006, the entire disclosure of which is hereby incorporated by reference.

FIELD OF THE INVENTION

The present invention is directed to an aqueous composition including a synergist combination of thidiazuron and diuron. The invention is also directed to a method of treating plants with an aqueous composition including a synergistic mixture of thidiazuron and diuron as a defoliant and without the use of organic solvents.

BACKGROUND OF THE INVENTION

One commercial defoliant product containing thidiazuron and diuron is sold under the tradename Ginstar by Bayer CropScience. This product is typically used for applying to cotton plants in an attempt to cause the leaves to fall off before the cotton is collected. Defoliants are often used to control plant growth. In the harvesting of cotton, defoliants are often applied to the cotton plants to cause the leaves to drop without adversely affecting the cotton boll. In this manner, the cotton can be harvested by machinery without contaminating the cotton with the leaves from the plant.

The activity of thidiazuron in the Ginstar product is believed to be due to the solvents used to disperse and spray the active ingredients. Numerous researchers have attempted to combine two active ingredients together at the same concentration. The results have not been able to obtain the same activity as thidiazuron alone or the product sold under the tradename Ginstar. Thidiazuron is very insoluble in many solvents, and thus, requires a mixture of exotic and expensive organic solvents and cosolvents. It is believed that these organic solvents contribute to the activity of the thidiazuron and its effectiveness as a defoliant. Ginstar is an emulsion concentrate containing 1-octyl-2-pyrrolidone and 1-dodecyl-2-pyrrolidone as essential solvents for producing the emulsion concentrate. The emulsion concentrate is mixed with water and applied to the plants as an emulsion. The organic solvents of Ginstar are highly toxic and dangerous to handle. The organic solvents are also believed to contribute to the sticky nature of Ginstar.

The Ginstar product has a disadvantage of producing a quick burn when applied to cotton leaves caused by the organic solvents. This causes the leaves to exhibit phytotoxicity that promotes the leaves to remain stuck on the plant rather than drop to the ground quickly. The solvents are believed to prevent the middle lamella from being fully dissolved, thereby preventing the leaves from falling quickly. A longer period of time is required for the leaves to fall from the plant naturally by gravity, wind and the like, since the desiccated leaves are not as heavy as non-desiccated leaves. The leaves that remain on the cotton plant are then incorporated into the harvested cotton and are processed during the ginning process. The small bits of leaves are then incorporated in the finished product and lower the quality of the cotton lint for the production of cotton goods such as clothes.

The action of thidiazuron affects the middle lamella of the cotton stem and dissolves the stem over a few days. This weakens the stem so that the leaves fall free from the plant thereby avoiding the problem of leaves being stuck to the plant and the quality issue as a result of the leaves remaining on the plant. The thidiazuron of Ginstar is sold as a stand alone defoliant. The thidiazuron is used at rates of 0.05 to 0.01 lbs. active ingredient per acre. Ginstar is used at rates of 0.0625 to 0.03125 lbs. active ingredient per acre. The organic solvents of Ginstar are believed to desiccate the leaves which prevents the middle lamella of the leaves from fully dissolving, which can prevent the leaves from falling off. Ginstar is not suitable for use in several of the U.S. cotton production areas as a result of the problems of the leaves remaining on the cotton plant. Ginstar is also highly sensitive to the rate used and the variety of the plants where it is applied.

Accordingly, there is a continuing need in the industry for an improved defoliant composition.

SUMMARY OF THE INVENTION

The invention is directed to a defoliating composition for defoliating vegetation. The invention is also directed to a method of treating vegetation and defoliating plants by applying the composition in an amount effective to defoliate the plants. The invention is particularly directed to a method and composition for treating cotton plants.

The invention relates to the discovery that an aqueous composition can be produced including the combination of a pre-emergence herbicide with a defoliant to enhance the efficacy of the defoliant. The invention is particularly directed to the discovery that an aqueous suspension or slurry including the combination of thidiazuron and diuron exhibit an enhanced activity and particularly an enhanced defoliating activity compared to the prior compositions containing organic solvents. The combination of the components have been found to be more effective than the components used individually. The resulting combination has been found to exhibit a synergism since the combination exhibits a level of activity that is greater than expected when used in similar amounts. The combination has been found to be particularly effective in treating cotton plants for promoting defoliation.

The various aspects of the invention are directed to an aqueous composition comprising thidiazuron and diuron with a surfactant to suspend the actives in the aqueous medium. The diuron is included in an amount effective to enhance the efficacy of the thidiazuron and to prevent regrowth of the leaves. The aqueous composition is an aqueous suspension or slurry in the absence of organic solvents. The thidiazuron and the diuron are present as solid particles having a particle size sufficiently small to remain in suspension in an aqueous medium.

The aspects of the invention are further provided by a method of controlling vegetation by applying an aqueous composition to the vegetation in an amount effective to treat the vegetation, where the composition comprises thidiazuron and diuron. The method of the invention is particularly effective in defoliating vegetation such as cotton.

These and other aspects of the invention will become apparent from the following details description of the invention which discloses various embodiments of the invention.

DETAILED DESCRIPTION OF THE INVENTION

The present invention is directed to an aqueous composition and a method for treating plants using the aqueous composition. The present invention is particularly directed to an aqueous defoliant composition including a mixture of thidiazuron and diuron. The composition includes a surfactant to suspend the actives in the aqueous medium. The invention is also directed to a method of defoliating plants by applying an effective amount of a composition to plants where the composition contains a mixture or blend of thidiazuron and diuron. The aqueous composition in one embodiment includes thidiazuron alone or a mixture of thidiazuron and diuron in combination with an effective amount of a surfactant, dispersing agent, emulsifying agent, and other additives.

One aspect of the invention is the discovery that a synergistic effect is obtained using a combination of thidiazuron and diuron for use as a defoliant. The synergistic mixture is particularly suitable for applying to cotton plants to cause the leaves to fall from the plant to enable cleaner harvesting of the cotton lint without contamination of the cotton lint by the leaf particles.

The aqueous composition containing the active components can be used for control of most forms of vegetation. The composition is particularly suitable as a defoliating agent for vegetation such as trees, fruits, and vegetables. The composition of the invention has been found to be particularly useful for defoliating cotton plants prior to harvesting the cotton. The composition can be used alone or in combination with other active agents such as plant growth regulators, insecticides, fertilizers, and the like.

The composition of the invention is an aqueous composition where the actives are present in the form of a stable aqueous suspension or slurry. Thidiazuron and diuron are insoluble in water and have limited solubility in only a few known organic solvents. The actives of the invention are not dissolved or dispersed in organic solvents but rather are suspended in the aqueous medium as solid particles having a particle size distribution sufficiently small to remain in suspension and prevent the particles from falling out of suspension. Preferably, the actives have a narrow particle size distribution and have a sufficiently small median particle size to provide good coverage and distribution to the plants, thereby enhancing the efficacious uptake at more sites on the plant. The aqueous suspension or slurry of the invention includes the solid particles of thidiazuron and diuron and a surfactant in an amount sufficient to suspend the particles. The aqueous slurry or suspension can also include one or more wetting agents, emulsifiers, stabilizers and/or thickeners. The resulting suspension or slurry is a stable composition that can be diluted in water to the desired concentration for applying to the vegetation. The diluted composition includes the particles of thidiazuron and diuron in suspension which can be sprayed or applied to the vegetation by other known methods.

The composition of the invention is an aqueous suspension or slurry preferably in the absence of or substantially in the absence of an organic solvent. In particular, the composition is in the absence of 1-octyl-2-pyrrolidone and 1-dodecyl-2-pyrrolidone. As used herein, the term "organic solvent" refers to organic liquids in which thidiazuron and diuron are soluble or at least partially soluble or are present in small amounts insufficient to dissolve or solubilize the actives.

The aqueous suspension or slurry can contain organic liquids that function as surfactants, emulsifiers, thickeners, antifoam agents or antifreeze. For example, in one embodiment, the aqueous composition contains an antifreeze such as propylene glycol. Propylene glycol does not function as a solvent and is not capable of functioning as a solvent for thidiazuron or diuron. The antifreeze such as propylene glycol is preferably included in an amount of about 5 wt % or less.

The thidiazuron and diuron formulation of the invention can be used in various amounts to attain the desired defoliant properties. The aqueous composition is mixed with water and applied to the crops in an amount generally in the range of about 2 to 8 oz. of the aqueous suspension or slurry per acre. This corresponds to an application rate of about 0.02 to 0.20 pounds of the actives per acre. The application rate provides improved defoliating properties without the phytotoxicity and burnt leaves that remain on the plant as in the prior processes and formulations.

The term active ingredients as used herein refers to the amount of thidiazuron and diuron present in the formulation. The aqueous suspension or slurry typically includes the thidiazuron and diuron as actives in an amount of about 0.5 to 6 pounds per gallon. In one embodiment, the actives are present in the aqueous suspension or slurry in an amount of about 0.25 to 1.5 pounds per gallon. The aqueous thidiazuron and diuron suspension or slurry containing a surfactant avoids the problems associated with the prior processes using organic solvent by enabling more uniform absorption of the active ingredients so that the activity is directed to the middle lamella of the leaf stem to enable the leaves to fall from the plant. The aqueous formulation of the invention avoids the problems of the prior processes where the actives become absorbed by the leaf tissue which is unable to transport the actives through the plant. In addition, the formulation of the invention provides more consistent and thorough coverage when applied to mature leaf structure which has a heavy wax layer that protects the leaf and has more absorption sites available for uptake and subsequent activity. These features contribute to more of the active ingredients being absorbed by the plant and increased activity.

The formulation of the invention includes as actives a synergistic combination of thidiazuron and diuron suspended in the aqueous suspension or slurry. Thidiazuron is the common name for 1-phenyl-3-(1,2,3-thiadiazol-5-yl)-urea (CAS No. 51707-2). Diuron is the common name for 3-(3,4-dichlorophenyl)-1,1-dimethylurea (CAS No. 330-54-1). The ratio of the actives can vary depending on the plant and other growing conditions. In one embodiment, the ratio of the thidiazuron to diuron is about 1:1 to about 5:1 by weight, and preferably about 1:1 to 3:1 by weight. In one embodiment found to be particularly suitable for defoliating cotton plants, the thidiazuron to diuron ratio is about 2:1 by weight.

The formulation of one preferred form of the invention is a suspension concentrate prepared as an aqueous suspension or slurry containing the actives and a surfactant. The formulation can also include an emulsifier and a dispersant. It is believed that the surface active agents improve the spreading of the active ingredients to more sites at the plant leaf surface, thereby providing a higher degree of infiltration or penetration into the plant tissue. The surfactants also assist in maintaining the solid actives in suspension. In one embodiment, the suspension concentrate contains 1.5 pounds total actives per gallon. In another embodiment, the suspension concentrate contains 4.5 pounds total actives per gallon. The suspension concentrate generally contains about 1 to 5 pounds total actives per gallon. In other embodiments, the aqueous suspension or slurry contains about 12 wt % thidiazuron and about 6 wt % diuron.

In one form of the invention, the composition is a suspension concentrate which is prepared as an aqueous slurry where solids have a predetermined particle size to remain in suspension during storage and shipping. The suspension concentrate is diluted in water before use by the end user and applied to vegetation at the desired rate. The suspension concentrate is typically prepared by high shear mixing and milling equipment. One such method combines the water with the desired surfactants, emulsifying agents, biocides, antifreeze, antifoam agents and suspending agents in a mixer. The components are blended and the insoluble thidiazuron and diuron are added to form a homogenous slurry. The slurry is passed through a mill to obtain a desired particle size. In preferred embodiments, the thidiazuron and diuron actives are milled to a particle size sufficient to maintain the actives in suspension during storage and ultimate use by the end user. Preferably, the actives are milled to a median particle size of not greater than about 5 µm, and preferably not greater than 3 µm. Typically, the composition includes the actives having a median particle size of about 1 µm to about 5 µm, and preferably a median particle size of about 1 µm to 3 µm.

The slurry can be passed through a filter, such as a 100 µm filter, to remove foreign matter. Other additives such as wetting agents, emulsifying agents, dispersants, antifreeze, diluents, and the like, can be added to obtain the final concentrate.

The thidiazuron as used in the concentrate is a technical grade product which typically contains about 98.3% thidiazuron. The diuron is preferably diuron technical which typically contains about 98.4% diuron.

The concentrate can be used alone, although it is preferably diluted in water and applied to the vegetation. Additional wetting agents, surfactants, or carriers can be added, if desired. In other embodiments, the composition can be used with a solid carrier such as clay, talc, kaolin, limestone, and the like.

The suspension concentrate in one embodiment includes a butyl EO/PO block copolymer emulsifier and a dispersant having good wetting characteristics. One example of a suitable dispersant is a compound having a methacrylate backbone with PEG side chains sold under the tradename Altox 4913. An example of a suitable emulsifier or surfactant is sold under the tradename Atlas G-5000. One suitable emulsifier is a methacrylate having PEG side chains. The emulsifiers and dispersants are believed to contribute to the synergy with thidiazuron alone or a mixture of thidiazuron and diuron to enable efficient absorption by the plant without the use of toxic organic solvents. The emulsifier and the dispersant are generally included in an amount of about 2% to about 6% based on the weight of the concentrate. In one embodiment, the emulsifier and the dispersant are included in an amount of about 2% to about 4.5% based on the weight of the thidiazuron and diuron actives. Various other known and commercially available emulsifying agents, surfactants and thickeners can be used that are capable of suspending the actives in an aqueous medium without the use of organic solvents.

In one embodiment of the invention, the aqueous suspension concentrate includes about 12 wt % thidiazuron, about 6 wt % diuron, about 2 wt % surfactant, about 2 wt % dispersant with the balance being water. The concentrate also typically includes a biocide, an antifoam agent, an antifreeze and a suspending agent or thickener. In another embodiment, the aqueous suspension concentrate includes about 36 wt % thidiazuron, about 18 wt % diuron, about 2.5 wt % surfactant, about 2.3 wt % dispersant in an aqueous diluent.

An example of a suitable aqueous formulation according to the invention includes 12 wt % thidiazuron, 6 wt % diuron, 2.00 wt % Atlas G-5000, 2.00 wt % Altox 4913, a biocide, an antifoam, an antifreeze, and a thickener.

Another example of a formulation includes 36 wt % thidiazuron, 18 wt % diuron, 2.3 wt % Altox 4913, 2.0 wt % Atlas G-5000, an antifoam, a biocide, an antifreeze, and a thickener.

The synergistic combination of the active ingredients can also be used in combination with fungicides, insecticides, plant growth regulators, such as ethephon and other active agents.

The following non-limiting examples describe various aspects of the invention.

Example 1

In this Example, an aqueous concentrate was prepared by producing an aqueous carrier including an antifoam agent, a surfactant, an antibacterial agent and a dispersant. Thidiazuron technical and diuron technical were added to form an aqueous slurry. The slurry was milled to a median particle size of about 3 µm. A thickener and propylene glycol as an antifreeze were then added and mixed to form the aqueous concentrate. The final composition contained 12 wt % thidiazuron and 6 wt % diuron based on the total weight of the aqueous suspension composition and contained no organic solvents.

Example 2

In this Example, an aqueous suspension concentrate was produced as in Example 1 except for the amounts of the actives. In this Example, the aqueous concentrate contained 36 wt % thidiazuron, 18 wt % diuron, 2.3 wt % of a dispersant, 2.0 wt % of an emulsifier, an antifoam agent, biocide, antifreeze and thickener, with the balance water. The composition contained no organic solvents.

Example 3

In this Example, a mixture of the composition of Example 1 and ethephon was applied to cotton plants in four replications in four different fields in the Rio Grande Valley. The ethephon used was an aqueous mixture containing 6 pounds ethephon per gallon. The composition of Example 1 and the ethephon were diluted with water to produce a sprayable mixture. The resulting mixture was applied to the cotton plants in an amount of 32 oz. of the ethephon and 4 oz. of the composition of Example 1 per acre. The ethephon is the tradename for 2-chloroethyl-phosphonic acid which is used as a plant growth regulator to promote boll opening. The percent defoliation as measured by leaf drop and percent boll opening after 14 to 15 days were evaluated. The results are shown in Table 1.

TABLE 1

| Application | % Defoliation | % Open Boll |
| --- | --- | --- |
| 1 | 97 | 96 |
| 2 | 92 | 96 |
| 3 | 98 | 95 |
| 4 | 97 | 95 |
| average | 97.25 | 95.25 |

In this Example, a mixture of ethephon as in Example 1 and the product sold under the tradename Ginstar by Bayer CropScience which contains 12 wt % thidiazuron, 6 wt % diuron, 1-octyl-2-pyrrolidone and 1-dodecyl-2-pyrrolidone as an emulsion concentrate. The mixture was applied to the cotton plants in four replications in fields in the Rio Grande Valley. The mixture was applied at a rate of 32 oz. ethephon and 4 oz. Ginstar per acre. The percent defoliation and boll opening after 14 to 15 days were evaluated. The results are shown in Table 2.

TABLE 2

| Application | % Defoliation | % Open Boll |
| --- | --- | --- |
| 1 | 95 | 97 |
| 2 | 92 | 95 |
| 3 | 94 | 95 |
| 4 | 92 | 95 |
| average | 93.25 | 95.5 |

The results of Tables 1 and 2 show an improved defoliation by the aqueous composition of Example 1 compared to the emulsion concentrate of Ginstar when applied at the same rate while the boll opening effect was essentially unchanged.

Example 4

In the Example, the aqueous composition of Example 1 and emulsified concentrate of Ginstar are applied without the ethephon. The aqueous composition of Example 1 and Ginstar are applied to cotton plants at a rate of 4 oz. per acre. The percent defoliation and the percent boll opening after 14 days was recorded as shown in Table 3.

TABLE 3

| Application | % Defoliation | % Open Boll |
|---|---|---|
| Example 1 | 92 | 90 |
| Example 1 | 92 | 91 |
| average | 92 | 90.5 |
| Ginstar | 90 | 88 |
| Ginstar | 85 | 90 |
| average | 87.5 | 89.0 |

The results of Table 3 show an improved defoliation using the composition of Example 1 compared to Ginstar and an equivalent or slightly better boll opening.

Example 5

In this Example, a mixture of the composition of Example 1 and ethephon was applied to cotton plants in different replications in fields in the Rio Grande Valley. The mixture was applied in an amount of 32 oz. of the ethephon and 4 oz/of the composition of Example 1 per acre. The percent defoliation and percent open boll were recorded as in Table 4.

TABLE 4

| Application | % Defoliation | % Open Boll |
|---|---|---|
| 1 | 92 | 90 |
| 2 | 95 | 90 |
| 3 | 96 | 92 |
| average | 94.3 | 90.7 |

A mixture of ethephon and Ginstar was also applied to cotton plant in the fields in the same area and in the same amounts of 32 oz. ethephon and 4 oz. Ginstar per acre. The percent defoliation and percent open boll are recorded in Table 5.

TABLE 5

| Application | % Defoliation | % Open Boll |
|---|---|---|
| 1 | 85 | 85 |
| 2 | 95 | 91 |
| 3 | 90 | 90 |
| average | 90.00 | 88.7 |

This Example shows an improved defoliation of the aqueous composition of Example 1 compared with the emulsified concentrate of Ginstar.

Example 6

In this Example, a mixture of the composition of Example 1 and ethephon was applied to cotton plants in different replications in fields in the Rio Grande Valley. The mixture was applied in an amount of 32 oz. of the ethephon and 4 oz/of the composition of Example 1 per acre. The percent defoliation and percent open boll were recorded as in Table 6.

TABLE 6

| Application | % Defoliation | % Open Boll |
|---|---|---|
| 1 | 95 | 95 |
| 2 | 95 | 92 |
| 3 | 92 | 92 |
| 4 | 92 | 92 |
| 5 | 92 | 95 |
| 6 | 95 | 90 |
| average | 93.5 | 92.7 |

A mixture of ethephon and Ginstar was also applied to cotton plant in the fields in the same area and in the same amounts of 32 oz. ethephon and 4 oz. Ginstar per acre. The percent defoliation and percent open boll are recorded in Table 7.

TABLE 7

| Application | % Defoliation | % Open Boll |
|---|---|---|
| 1 | 95 | 92 |
| 2 | 94 | 90 |
| 3 | 92 | 92 |
| 4 | 92 | 90 |
| 5 | 90 | 92 |
| 6 | 92 | 90 |
| average | 92.5 | 91.0 |

While various embodiments of the invention have been described, it will become apparent to one skilled in the art that various changes and modifications can be made without departing from the scope of the invention as defined in the appended claims.

What is claimed is:

1. A composition for controlling vegetation comprising an aqueous suspension or slurry of thidiazuron, diuron, an emulsifier comprising alpha-butyl, omega hydroxy polyoxypropylene block copolymer with polyoxyethylene, and a dispersant comprising methyl methacrylate-methacrylic acid-monomethoxypolyethylene glycol methacrylate copolymer in an amount sufficient to maintain thidiazuron and diuron in suspension in an aqueous matrix; wherein the thidiazuron and diuron are present in a ratio of about 2:1 by weight wherein the composition has about 10 wt % to about 40 wt % thidiazuron and about 5 wt % to about 20 wt % diuron based on the total weight; wherein the alpha-butyl, omega hydroxy polyoxypropylene block copolymer with polyoxyethylene and the methyl methacrylate-methacrylic acid-monomethoxypolyethylene glycol methacrylate copolymer are each in an amount of about 2% to about 6% by weight; and wherein the composition is without added organic solvent.

2. The composition of claim 1, wherein said diuron is present in a synergistic amount to enhance the efficacy of the thidiazuron.

3. The composition of claim 1, wherein the composition further includes at least one component selected from the group consisting of a surfactant, wetting agents, thickening agents, and mixtures thereof.

4. The composition of claim 1, wherein the composition includes about 35 wt % to about 40 wt % thidiazuron and about 15 wt % to about 20 wt % diuron based on the total weight of the composition.

5. The composition of claim 1, wherein the thidiazuron and diuron have a median particle diameter of not greater than 5 μm.

6. The composition of claim 1, wherein the composition comprises about 10 wt % to about 40 wt % thidiazuron, about 5 wt % to about 20 wt % diuron, a surfactant, and the balance water, where the percentages are based on the total weight of the composition.

7. The composition of claim 1, wherein the composition is in the absence of 1-octyl-pyrrolidone and 1-dodecyl-2-pyrrolidone.

8. A method of defoliating vegetation comprising the step of applying an aqueous mixture to vegetation in an amount effective to defoliate the vegetation, wherein the mixture is obtained from an aqueous suspension or slurry comprising thidiazuron, diuron, an emulsifier comprising alpha-butyl, omega hydroxy polyoxypropylene block copolymer with polyoxyethylene, and a dispersant comprising methyl methacrylate-methacrylic acid-monomethoxypolyethylene glycol methacrylate copolymer; wherein the thidiazuron and diuron are present in a ratio of about 2:1 by weight wherein the composition has about 10 wt % to about 40 wt % thidiazuron and about 5 wt % to about 20 wt % diuron based on the total weight; wherein the alpha-butyl, omega hydroxy polyoxypropylene block copolymer with polyoxyethylene and the methyl methacrylate-methacrylic acid-monomethoxypolyethylene glycol methacrylate copolymer are each in an amount of about 2% to about 6% by weight; and wherein the aqueous suspension or slurry is without added organic solvent.

9. The method of claim 8, wherein the diuron is included in a synergistic amount to enhance the efficacy of the thidiazuron.

10. The method of claim 8, comprising applying the aqueous mixture in an amount of about 0.02 to 0.20 lbs total actives per acre.

11. The method of claim 8, wherein the vegetation is cotton plants.

12. The method of claim 8, wherein the aqueous suspension or slurry is in the absence of 1-octyl-pyrrolidone and 1-dodecyl-2-pyrrolidone.

13. A method of defoliating cotton plants comprising applying a mixture to the cotton plants in an amount effective to defoliate the cotton plants, wherein the mixture is obtained from an aqueous suspension or slurry comprising thidiazuron, a synergistic amount of diuron to enhance the efficacy of the thidiazuron, an emulsifier comprising alpha-butyl, omega hydroxy polyoxypropylene block copolymer with polyoxyethylene, and a dispersant comprising methyl methacrylate-methacrylic acid-monomethoxypolyethylene glycol methacrylate copolymer; wherein the thidiazuron and diuron are present in a ratio of about 2:1 by weight wherein the composition has about 10 wt % to about 40 wt % thidiazuron and about 5 wt % to about 20 wt % diuron based on the total weight; wherein the alpha-butyl, omega hydroxy polyoxypropylene block copolymer with polyoxyethylene and the methyl methacrylate-methacrylic acid-monomethoxypolyethylene glycol methacrylate copolymer are each in an amount of about 2% to about 6% by weight; and wherein the aqueous suspension or slurry is without added organic solvent.

14. The method of claim 13, wherein the composition is applied at a rate of about 0.02 to 0.20 lbs total actives per acre.

15. The method of claim 13, wherein the thidiazuron and diuron are present as solid particles and have a median particle size of not greater than 5 μm.

16. The composition of claim 1, wherein the alpha-butyl, omega hydroxyl polyoxypropylene block copolymer with polyoxyethylene and the methyl methacrylatemethacrylic acid-monomethoxypolyethylene glycol methacrylate copolymer are each in an amount of about 2% to about 4.5% by weight.

17. The method of claim 8, wherein the alpha-butyl, omega hydroxyl polyoxypropylene block copolymer with polyoxyethylene and the methyl methacrylatemethacrylic acid-monomethoxypolyethylene glycol methacrylate copolymer are each in an amount of about 2% to about 4.5% by weight.

18. The method of claim 13, wherein the alpha-butyl, omega hydroxyl polyoxypropylene block copolymer with polyoxyethylene and the methyl methacrylatemethacrylic acid-monomethoxypolyethylene glycol methacrylate copolymer are each in an amount of about 2% to about 4.5% by weight.

19. The composition of claim 1, wherein the total amount of thidiazuron and diuron is about 1 to 5 pounds per gallon.

20. The composition of claim 1, wherein the total amount of thidiazuron and diuron is about 1.5 pounds per gallon.

21. The composition of claim 1, wherein the composition has about 12 wt % thidiazuron and about 6 wt % diuron based on the total weight.

22. The method of claim 8, wherein the mixture has about 12 wt % thidiazuron and about 6 wt % diuron based on the total weight.

23. The method of claim 13, wherein the mixture has about 12 wt % thidiazuron and about 6 wt % diuron based on the total weight.

\* \* \* \* \*